United States Patent [19]

Deigin et al.

[11] Patent Number: 5,736,519
[45] Date of Patent: Apr. 7, 1998

[54] PEPTIDE, A METHOD FOR ITS PREPARATION AND A PHARMACEUTICAL COMPOSITION CONTAINING THE PEPTIDE

[76] Inventors: Vladislav I. Deigin, 42 Fenn Avenue, North York Ontario, Canada, M2L 1M8; Andrei Marxovich Korotkov, c/o Can-Bramar Limited, 1300 Don Mills Road, 2nd Floor, West Entrance, Toronto Ontario, Canada, M3B 2W6

[21] Appl. No.: 657,888

[22] Filed: Jun. 7, 1996

[51] Int. Cl.$^6$ ............. A61K 38/00; A61K 38/04; A61K 38/06; C04K 5/00
[52] U.S. Cl. ............. 514/18; 514/17; 514/19; 530/330; 530/331
[58] Field of Search ............. 530/330, 331; 514/17, 18, 19

[56] References Cited

PUBLICATIONS

Yakoylev et al.; Glutampltryptophan For Treating Immunodeficiency Conditions; WO8906134 A1; Jul. 13, 1989; 1–20 (Abstract).

Semina et al.; The Radioprotective Effect of Synthetic Immunomodulators on Hemopoietic CFU–S; Radiatsionnya Biologiya Radioekologiya 33(3) 1993. 808–811 (Abstract).

*Primary Examiner*—Cecilia J. Tsang
*Assistant Examiner*—Jennifer Harle
*Attorney, Agent, or Firm*—Merchant, Gould, Smith, Edell, Welter & Schmidt, P.A.

[57] ABSTRACT

A peptide of the formula I

X-A-D-Trp-Y wherein X is hydrogen, glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, α-aminobutyric acid or ξ-aminocaproic acid; A is D-glutamic acid or iD-glutamic acid; and Y is glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophn, α-aminobutyric acid, ξ-aminocaproic acid, hydroxyl, or $C_1$–$C_3$ substituted amide.

6 Claims, No Drawings

PEPTIDE, A METHOD FOR ITS PREPARATION AND A PHARMACEUTICAL COMPOSITION CONTAINING THE PEPTIDE

FIELD OF THE INVENTION

The invention relates to a biologically active peptide; a novel pharmaceutical composition containing the peptide; a method of preparing the peptide; and uses of the peptide.

BACKGROUND TO THE INVENTION

Radiotherapy and chemotherapy are well established treatment methods for malignant disease. Cells which grow and divide rapidly are most vulnerable to the effects of radiation and cytotoxic agents. Among those affected are tumor cells, and normal cells including hair and intestinal cells, and cells of the hemopoietic and immune systems. Damage to normal cells of the hemopoietic and immune systems by radiation and cytotoxic agents often has life-threatening consequences, and it limits the ability to administer a full therapeutic dose.

There has been extensive research to identify agents which will protect normal hemopoietic and immunologic cells from the effects of radiotherapy and chemotherapy, or aid in the reconstitution of cells suppressed by these therapies. For example, transforming growth factor beta-1 has been reported to be useful for protecting hematopoietic stem cells from the myelotoxicity of chemotherapeutic drugs or radiation therapy (U.S. Pat. No. 5,278,145 to Keller et al.). A lyophilised composition containing human albumin in thymosin alpha 1 was also reported to exert a preventative activity against progression of leukemias in mice whose immune systems were severely damaged by treatment with cytostatic agents or radiation treatment (89EP 102569 to Lattanzi). Hemopoietic growth factors such as interleukin-3 and CSF have been used to potentiate the immune response or assist in reconstituting normal blood following radiation- or chemotherapy-induced hematopoietic cell suppression (WO8805469 to Anderson et al., U.S. Pat. No. 4,959,455 to Ciarletta et al; U.S. Pat. No. 4,999,291).

SUMMARY OF THE INVENTION

Broadly stated, the present invention relates to a peptide of the formula I

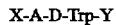

$$X\text{-}A\text{-}D\text{-}Trp\text{-}Y \qquad (I)$$

wherein X is hydrogen, glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, α-aminobutyric acid, or ξ-aminocaproic acid; A is D-glutamic acid, or iD-glutamic acid; and Y is glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, α-aminobutyric acid, ξ-aminocaproic acid, hydroxyl or ($C_1$–$C_3$) substituted amide.

The invention also relates to analogues of the peptides of the invention and cyclized peptides. The terms "peptide" and "peptides" used herein include these analogues and cyclized peptides.

The invention also contemplates a process for preparing the peptides using a method which results in a good yield, with simple and efficient steps.

The peptides of the invention have been shown to be non-toxic: and to enhance the reconstitution of cells of the hemopoietic and immune systems after the cells are exposed to radiation or chemotherapeutic agents.

Therefore, the present invention relates to a pharmaceutical composition comprising one or more of the peptides of the invention and a pharmaceutically acceptable carrier. The pharmaceutical composition may be used to enhance reconstitution of cells of the hemopoietic and immune systems in a subject following radiation-or chemotherapy-induced suppression of the cells.

The invention still further relates to a method of enhancing reconstitution of cells of the hemopoietic and immune systems in a subject following radiation-or chemotherapy-induced suppression of the cells comprising administering to the patient an amount of a peptide of the invention effective to enhance reconstitution of the cells.

The invention also contemplates a method of treating a subject following radiation or chemotherapy comprising administering to the patient an amount of a peptide of the invention effective to enhance reconstitution of cells of the hemopoietic and immune systems in the subject.

Additional objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from the detailed description.

DETAILED DESCRIPTION OF THE PREFERRED EMBODIMENT

The following standard abbreviations for the amino acid residues are used throughout the specification: Ala—alanine; Glu—glutamic acid; Phe—phenylalanine; Gly—glycine; Ile—isoleucine; Leu—leucine; Pro—proline; Val—valine; NVal—N-valine; Trp—tryptophan; and Tyr—tyrosine.

As mentioned previously, the present invention relates to a peptide of the formula I

$$X\text{-}A\text{-}D\text{-}Trp\text{-}Y \qquad (I)$$

wherein X is hydrogen, glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, α-aminobutyric acid, ξ-aminocaproic acid; A is D-glutamic acid or iD-glutamic acid; and Y is glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, α-aminobutyric acid, ξ-aminocaproic acid, hydroxyl or $C_1$–$C_3$ substituted amide.

In an embodiment of the invention, in the peptide of the formula I, X is hydrogen, A is D-glutamic acid or iD-glutamic acid, and Y is OH or a $C_1$–$C_3$ substituted amide.

Preferred peptides of the invention have the sequence H-D-Glu-D-Trp-OH and H-iD-Glu-D-Trp-OH.

The peptides of the invention may additionally be characterized by the following physical and chemical properties: a yellowish-white or grey powder, soluble in water, moderately soluble in alcohol, and insoluble in chloroform. The UV spectrum in the range of 250–300 nm has a maximum at 280±2 nm, and a shoulder at 287±2 nm.

The peptides of the invention may also include analogues of the peptide of the Formula I which may include, but are not limited to the peptide of the Formula I containing one or more amino acid insertions. Amino acid insertions may consist of a single amino acid residue or sequential amino acids. Analogues of the peptide of the invention exhibit the activity of the peptide and may further possess advantageous features such as increased bioavailability, stability, or reduced host immune recognition.

The invention includes cyclic derivatives of the peptides of the invention. Cyclization allows the peptide to assume a more favourable conformation. Cyclization of the peptides may be achieved using techniques known in the art. In particular, disulphide bonds may be formed between two appropriately spaced components having free sulfhydryl groups. The bonds may be formed between side chains of amino acids, non-amino acid components or a combination of the two.

Peptides of the present invention may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and tolunesulphonic acids.

The peptides of the invention may be synthesized by preparing the glutamyl containing peptides in solution by opening the internal anhydride of tetrabutyloxycarbonyl-glutamine (D or L) acid using the corresponding D-Trp-Y derivative, followed by chromatographic separation of α-and γ-isomers, and further chain building with the use of activated ethers or mixed anhydrides of protected amino acids. The method of preparation of the peptides will be better understood in light of the examples discussed later herein.

The peptides of the present invention may also be prepared by chemical synthesis using techniques known in the chemistry of proteins such as solid phase synthesis, (for example see Merrifield, 1964, J. Am. Chem. Assoc. 85:2149–2154), and purified by HPLC of protected peptides. In addition the peptides may be prepared by conventional recombinant DNA techniques.

The peptides of the present invention may be used to enhance reconstitution of cells of the hemopoietic and immune systems (e.g. stem, myeloid, erythroid, lymphoid, or megakaryocyte cells, or mature myeloid or lymphoid cells, or combinations thereof) in a subject following radiation-or chemotherapy-induced suppression of the cells.

Therefore, the peptides of the present invention may be formulated into pharmaceutical compositions for administration to subjects in a therapeutically active amount and in a biologically compatible form suitable for in vivo administration, ie. a form of the peptides to be administered in which any toxic effects are outweighed by the therapeutic effects.

The peptides may be administered to animals preferably humans in a therapeutically active amount. A therapeutically active amount is defined as an amount of the active ingredient, i.e., peptide, effective, at dosages and for periods of time necessary to achieve the desired result i.e. reconstitution of cells of the hemopoietic and immune systems. A therapeutically active amount of a peptide may vary according to factors such as disease state, age, sex, and weight of the individual. Dosage regime may be altered to provide the optimum therapeutic response. Generally, the daily regimen should be in the range of 200–1000 µg of peptide.

The peptides may be administered by any means known in the art. Because the desired targets of the peptides occur primarily in the bone marrow and blood system it is desirable to reach those tissues. The peptides can be administered either parenterally, intravenously or subcutaneously. Depending upon the route of administration, the peptides in the pharmaceutical compositions may be coated in a material to protect them from the action of enzymes. Organic substances may also be included in the compositions to prolong the pharmacologic actions of the peptides. Examples of such organic compositions include non-antigenic gelatin, carboxymethylcellulose, sulphonate, or phosphate ester of alginic acid, dextran, polyethylene glycol and other glycols, phytic acid, polyglutamic acid, and protamine.

The pharmaceutical compositions of the invention can be prepared by per se known methods for the preparation of pharmaceutically acceptable compositions which can be administered to subjects, such that an effective quantity of peptide is combined in a mixture with a pharmaceutically acceptable vehicle. Examples of pharmaceutically acceptable vehicles are described in Remington's Pharmaceutical Sciences (Remington's Pharmaceutical Sciences, Mack Publishing Company, Easton, Pa., USA 1985).

Compositions for injection include, albeit not exclusively, the peptides in association with one or more pharmaceutically acceptable vehicles or diluents, and contained in buffered solutions with a suitable pH and iso-osmotic with the physiological fluids. Any pharmaceutically suitable diluent can be used in the composition for injections: distilled water, physiological or a salt solution, and/or a buffer solution. The composition for injections may be prepared by conventional volume-weight procedures. A certain amount of the peptide is diluted to the necessary volume with a diluent or solvent. The solution is then filtered through sterilized filters, bottled or ampouled. The resultant solution is a stable transparent liquid, and does not contain any chemical or other impurities.

Solid form preparations for oral administration can be made in the form of tablets, powders, or capsules. It may contain a medium for the active substance and other additives, including dyes, aromas, etc.

The compositions and treatments are indicated as therapeutic agents or treatments either alone or in conjunction with other therapeutic agents or other forms of treatment. In particular, the compositions of the invention may be used in combination with radiotherapy or chemotherapy, such as multi-drug chemotherapy or combination radiotherapy, and chemotherapy. The pharmaceutical composition may also be administered in conjunction with other agents which enhance reconstitution of hemopoietic and immune cells such as growth factors.

The present inventor has also found that the peptide of the invention increased the survival of animals receiving allogenic bone marrow transplants and may have immunosuppressant effects. Therefore, as yet another aspect of the invention, a method and pharmaceutical composition for increasing the survival of a subject of a transplant, preferably an allogenic transplant is provided comprising administering to the subject an amount of a peptide of the invention effective to increase the survival of the subject.

The following non-limiting examples are illustrative of the present invention.

EXAMPLE 1

Preparation of H-iD-Glu-D-Trp-OH a. Preparation of Boc-D-Glu-OH 14.7 g (0.1 Mol) of H-D-Glu-OH was dissolved in 200 ml of distilled water, and the pH was adjusted to 10.2 with 0.1M potassium hydroxide. 33.0 g (0.3 Mol) of BOC₂O in dioxane was added with intensive mixing. The pH was controlled using pH-stat. After completion of the reaction, the mixture was transferred to a separating funnel, and extraction was carried out from the alkaline solution with ethyl acetate (3×150 ml). The pH of the aqueous phase was adjusted to 3.0 using 0.2% sulphuric acid, and Boc-D-Glu-OH was extracted from the organic phase (3×200 ml). The organic phase was washed three times with 200 ml of $Na_2SO_4$ saturated solution to neutral pH, and dried over $Na_2SO_4$, and evaporated to oil under vacuum. The yield was 16.7 g (68%).

b. Preparation of Boc-D-Glu-D-Trp-OH and Boc-iD-Glu-D-Trp-OH mixture 16.7 g (0.068 Mol) Boc-D-Glu-OH was dissolved in 200 ml dimethyl formamide cooled to 0° C., and 20.6 g (0.1 Mol) N,N'-dicyclohexylcarbodiimide in 100 ml dimethyl formamide was added to the solution. The mixture was stirred at 4° C. for 4 h, and then was stored at room temperature for 8 h. The precipitate of dicyclohexyl carbamide was filtered, and washed twice with 50 ml dimethyl formamide. The filtrate was concentrated by evaporation under vacuum to ½ volume, cooled to 4° C., and to this was added 24.3 g (0.1 Mol) H-D-Trp-OH with vigorous mixing. The solution was allowed to warm to room temperature. Completion of the reaction was carried out by TLC in the system of chloroform:ethyl acetate:methanol=6:3:1 by disappearance of the spot of internal anhydride of Boc-D-Glu acid. The remaining dihexyl carbamide was separated by filtration and evaporation under vacuum. The resultant residue was a thick oil. 200 ml ethyl acetate and 200 ml of 0.2% sulphuric acid solution were added to the residue. The organic layer was separated, washed with $Na_2SO_4$ saturated solution to neutral pH, and dried over $Na_2SO_4$. The residue was further dried by evaporation under vacuum. The resultant oil-like precipitate was a mixture of Boc-D-Glu-D-Trp-OH and Boc-iD-Glu-Trp-OH. Total yield of the mixture was 25.4 g (70%).

c. Preparation of H-D-Glu-D-Trp-OH and H-D-iGlu-D-Trp-OH mixture 25.4 g of the Boc-D-Glu-Trp-OH and Boc-iD-Glu-Trp-OH mixture (0.048 Mol) was dissolved in 200 ml of formic acid, and stirred for 1 h at 40° C. The solvent was evaporated under vacuum to a thick oil.

The peptides were separated and purified by ion exchange chromatography in a Sephadex SP-PEA column in a gradient of 0.01–0.2M pyridine acetate buffer. Yield was 5.7 g (35%) of H-D-Glu-D-Trp-OH and 5.7 g (35%) of H-iD-Glu-D-Trp-OH.

The resultant peptide has the following physical and chemical properties and characteristics:

Primary structure—H-iD-Glu-D-Trp-OH

Empirical formula—$C_{16}H_{20}N_3O_5$

Molecular weight—334.35

Appearance—yellowish-white or grey powder

Solubility—readily soluble in water, moderately soluble in alcohol, insoluble in chloroform.

UV-spectrum in the range 250–300 nm has the maximum at 280±2 nm and a shoulder at 287±2 nm.

$Rf_1$=0.30 (chloroform-methanol-32% acetic acid= 60:45:20) and $Rf_2$=0.52 (butanol-pyridine-water-acetic acid=5:5:4:1).

EXAMPLE 2

Table 1 presents physical and chemical characteristics of some analogues of the peptide of the formula I. $R_{f1}$ in the system (chloroform:methanol:32% acetic acid=60:45:20) and $R_{f2}$ in the system (butanol:pyridine:water:acetic acid= 5:5:4:1).

TABLE 1

| Peptide | Rf₁ | Rf₂ |
| --- | --- | --- |
| H—D—Glu—D—Trp—OH | 0.36 | 0.56 |
| H—iD—Glu—D—Trp—OH | 0.30 | 0.52 |
| H—iL—Glu—D—Trp—OH | 0.30 | 0.52 |
| Ala—D—Glu—D—Trp—OH | 0.34 | 0.61 |
| Ala—ID—Glu—D—Trp—OH | 0.32 | 0.55 |
| ξ-aminocaproyl-D—Glu—D—Trp—OH | 0.31 | 0.52 |
| ξ-aminocaproyl-iD—Glu—D—Trp—OH | 0.28 | 0.49 |
| H—D—Glu—D—Trp—Lys | 0.27 | 0.50 |
| H—iD—Glu—D—Trp—Lys | 0.24 | 0.46 |
| Leu—D—Glu—D—Trp—OH | 0.35 | 0.62 |
| Leu—iD—Glu—D—Trp—OH | 0.27 | 0.57 |

EXAMPLE 3

The biological effect of iD-Glu-D-trp was studied in Balb/c mice. Splenic cells of the mice were suspended in RPMI 1640 medium with 2 ml glutamine and 5% inactive fetal serum, and then dispensed into flat bottomed plates: 100 μl, 200,000 cells per well. The preparation under study was added at the beginning of cultivation. Concanavalin A was used as a mitogen, in a final concentration of 2 μg per well. The plates were incubated at 37° C. and in 5% $CO_2$ for 48 h. ³H-thymidine was incorporated into the cells in the amount of 5 mcsi/ml. 24 h prior to the end of cultivation. Proliferation of the cells was measured with the use of a scintillation c-counter and expressed in counts per minute (CPM). The results are shown in Table 2. The results were compared with mice treated in the same manner, but with cyclosporin A, instead of the peptide.

TABLE 2

| | CPM* Preparation dose (mcg/ml) | | | |
| --- | --- | --- | --- | --- |
| Preparation | 1 | 5 | 10 | 20 |
| iD—Glu—D—Trp | 68594 | 63428 | 20043 | 13222 |
| Cyclosporin A | 67649 | 2698 | 574 | 569 |
| Control | | 61467 | | |

*average value of three measurements

It can be seen that mice treated with the peptide showed a substantially increased activity over mice treated with cyclosporin A.

EXAMPLE 4

Radiotherapeutic Action of H-iD-Glu-D-Trp-OH

Radiotherapeutic action of H-iD-Glu-D-Trp-OH and its effect on the regeneration of hemopoietic progenitor cells was measured in studies of 1860 female mice, (CBA× C57BL) F1, aged 2 months, weighing about 20 g. Irradiation was carried out using a radiotherapeutic apparatus "Luch" with γ-rays in a dose of 0.85 Gr/min. The effect of the peptide on the population of colony forming units of spleen (CFU-S) was measured by the methods of spleen exo and endocolonies. The survival of mice irradiated in the dose of 8.5 Gr was observed for 30 days.

A relationship was found between the amount of peptide and colony yield from bone marrow irradiated in a dose of 1 Gr. The results are shown in Table 3. The suspension of bone marrow was irradiated in vitro in a dose of 1 Gr, and was immediately thereafter injected into the subject mice which had been irradiated in a dose of 8 Gr. Thirty minutes later, the subject mice were intravenously injected with the peptide in the amount shown in Table 3. In all doses tested, administration of the peptide increased the average colony yield from irradiated bone marrow. The largest increase was observed with a dose of 10 µg/kg of the peptide.

TABLE 3

| Irradiation dose | Peptide, mcg/kg | Number of mice | Average colony count $M \pm m$ | |
|---|---|---|---|---|
| — | — | 19 | 11,6 ± 1,1 | |
| 1 Gr | — | 20 | 4,4 ± 0,4 | |
| 1 Gr | 2,5 | 20 | 7,6 ± 0,4 | p < 0,01 |
| 1 Gr | 10,0 | 20 | 8,5 ± 0,8 | p < 0,01 |
| 1 Gr | 25,0 | 20 | 8,0 ± 0,6 | p < 0,01 |
| 1 Gr | 50,0 | 12 | 7,7 ± 0,8 | p < 0,05 |
| 1 Gr | 100,0 | 20 | 7,1 ± 0,8 | p < 0,05 |
| 1 Gr | 200,0 | 20 | 8,1 ± 0,7 | p < 0,05 |
| 1 Gr | 500,0 | 12 | 7,4 ± 0,8 | p < 0,05 |

EXAMPLE 5

The peptide H-iD-Glu-D-Trp-OH was found to increase survival of hemopoietic progenitor cells after their exposure to radiation doses in the amount of 0.5 to 3 Gr, in vivo. The results are shown in Table 4. In all cases of the mice being irradiated with a dose of 0.5 to 2 Gr, administration of the peptide increased the average colony yield from bone marrow, in some cases by a factor of almost two.

TABLE 4

| Irradiation dose | Peptide, mcg/kg | Number of mice | Average colony count $M \pm m$ | |
|---|---|---|---|---|
| — | — | 27 | 11,4 ± 0,9 | |
| 0,5 Gr | — | 12 | 7,8 ± 0,5 | |
| 0,5 Gr | 10 | 12 | 9,4 ± 0,5 | p < 0,05 |
| 1 Gr | — | 20 | 4,4 ± 0,4 | |
| 1 Gr | 10 | 20 | 8,5 ± 0,8 | p < 0,05 |
| 2 Gr | — | 30 | 2,7 ± 0,3 | |
| 2 Gr | 10 | 12 | 3,7 ± 0,1 | p < 0,05 |
| 3 Gr | — | 11 | 1,6 ± 0,2 | |
| 3 Gr | 10 | 12 | 1,5 ± 0,3 | |

EXAMPLE 6

Radiotherapeutic properties of the peptide H-iD-Glu-D-Trp-OH were investigated under conditions of irradiation in vivo. The effect of the peptide on regeneration of the CFU-S population in the bone marrow of irradiated mice was studied. The studied mice were irradiated in a dose of 4 Gr, and administered a 10 µg/kg dose of the peptide by intravenous injection according to the following schedule: once, an hour after irradiation; twice, an hour after irradiation and a day after irradiation; thrice, an hour after irradiation, and one day and two days after irradiation; 4 times, an hour after irradiation, and one, two and three days after irradiation. CFU-S count was measured on days 4, 7 and 11 after irradiation. On these days, at least 5 mice were killed, and their bone marrow was removed and injected into lethally irradiated recipients. During the seven days after irradiation in a dose of 4 Gr, the peptide aided in more intensive regeneration of CFU-S population. However, by the eleventh day, the peptide's effect had weakened.

EXAMPLE 7

The effectiveness of the peptide H-iD-Glu-D-Trp-OH in correction of cytopenias caused by chemical cytostatics was studied. Twenty four mice were administered with Ara-C, which is widely used in oncological practice, three times, at 24 h intervals. One hour after the last injection, treatment with the peptide was commenced on twelve of the mice. Seven days after the last Ara-C injection, the bone marrow of each of the mice was examined for karyocyte count, as well as for the content of hemopoietic progenitor cells (CFU-S-8 and CFU-S-12). The results are presented in Table 5. It can be seen that the mice treated with the peptide showed an increased karyocyte count by a factor of greater than two over those administered only Ara-C. Further, the mice administered the peptide showed an increased CFU-S-8 by a factor of almost three over those treated only with Ara-C, and an increased CFU-S-12 count by a factor of greater than two over those mice treated only with Ara-C. These results show the stimulating effect of the peptide on regeneration of the hemopoietic and immune systems, and suggest that the peptide is a promising agent in oncological practice.

TABLE 5

| Group | Karyocyte count × $10^6$ | CFU-S-8 | CFU-S-12 |
|---|---|---|---|
| Control | 18,5 ± 2,7 | 2053 ± 203 | 1887 ± 110 |
| Ara—C | 7,7 ± 1,2* | 493 ± 26* | 639 ± 54* |
| Ara—C + peptide | 18,8 ± 1,2 | 1391 ± 94 | 1379 ± 134 |

*trustworthiness was calculated as applied to this group, p < 0.05, each group consisted of 12 mice.

The effect of the peptide on the development of secondary disease after transplantation of allogenic bone marrow was investigated. With two different schedules of peptide injections, the 45 day survival rate of tested mice almost doubled when compared with the control population. In addition, based on weight loss of the mice under investigation, secondary diseases were progressing at a rate of about two weeks slower in mice treated with the peptide. On day 45, spleen weight of surviving mice exceeded that in the control population.

EXAMPLE 8

An acute toxicity study of the peptide H-iD-Glu-D-Trp-OH was carried out in compliance with the methodical recommendations of the Pharmacological Committee of the RF "Requirements to Preclinical Study of General Toxic Action of New Pharmacological Substances", M., 1985. According to the results of the study, intramuscular injection of a 1000-fold dose of the peptide did not cause an acute toxic effect.

It will be appreciated that various changes may be made within the spirit of the described invention, and all such changes are within the scope of the appended clam.

All publications, patents and patent applications referred to herein are hereby incorporated by reference in their entirety to the same extent as if each individual publication, patent or patent application was specifically and individually indicated to be incorporated by reference in its entirety.

We claim:

1. A peptide of the formula I

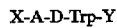  (I)

wherein X is selected from the group consisting of hydrogen, glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, α-aminobutyric acid, and ξ-aminocaproic acid; A is selected from the group consisting of D-glutamic acid and iD-glutamic acid; and Y is selected from the group consisting of glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tyrptophan, α-aminobutyric acid, ξ-aminocaproic acid, hydroxyl and $C_1$ to $C_3$ substituted amide.

2. A peptide of the formula I as claimed in claim 1 wherein X is hydrogen, A is iD-glutamic acid, and Y is selected from the group consisting of hydroxyl and $C_1$ to $C_3$ substituted amide.

3. A peptide having the sequence H-iD-Glu-D-Trp-OH.

4. A pharmaceutical composition comprising at least one of the peptides of the formula I as claimed in claim 1 and a pharmaceutically acceptable vehicle.

5. A method of enhancing reconstitution of cells of the hemopoietic and immune systems in a subject following radiation-or chemotherapy-induced suppression of the cells comprising administering to the patient an amount of a peptide of claim 1 effective to enhance reconstitution of the cells.

6. A method of treating a subject following radiation or chemotherapy comprising administering to the patient an amount of a peptide of claim 1 effective to enhance reconstitution of cells of the hemopoietic and immune systems in the subject.

* * * * *

UNITED STATES PATENT AND TRADEMARK OFFICE
CERTIFICATE OF CORRECTION

PATENT NO. : 5,736,519

DATED : April 7, 1998

INVENTOR(S) : Deigin et al.

It is certified that error appears in the above-identified patent and that said Letters Patent is hereby corrected as shown below:

On the title page, col. 1 insert item [30] as follows:

—[30] Foreign Application Priority Data
June 7, 1995 [RU] Russia........N 95108559/04/015649—.

Signed and Sealed this

Fifteenth Day of September, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,736,519
APPLICATION NO. : 08/657888
DATED : April 7, 1998
INVENTOR(S) : Vladislav I. Deigin and Andrei Marxovich Korotkov It is certified that error appears in the above-identified patent and that said Letters Patent is hereby corrected as shown below:

On Title page Item (57)

Abstract "iD-glutamic acid" should read -- γD-glutamic acid --;

Column 1, line 52 "iD-glutamic acid" should read -- γD-glutamic acid --;

Column 2, lines 49 "iD-glutamic acid" should read -- γD-glutamic acid --, 57 "iD-glutamic acid" should read -- γD-glutamic acid --, 59 "H-iD-Glu-D-Trp-OH" should read -- H-γD-Glu-D-Trp-OH --;

Column 4, line 64 "H-iD-Glu-D-Trp-OH" should read -- H-γD-Glu-D-Trp-OH --;

Column 5, lines 12 "Boc-iD-Glu-D-Trp-OH" should read -- Boc-γD-Glu-D-Trp-OH -- 35 "Boc-iD-Glu-Trp-OH" should read -- Boc-γD-Glu-Trp-OH--, 37 "H-D-iGlu-D-Trp-OH" should read -- H-D-γGlu-D-Trp-OH --, 40 "Boc-iD-Glu-Trp-OH" should read -- Boc-γD-Glu-Trp-OH --, 47 "H-iD-Glu-D-Trp-OH" should read -- H-γD-Glu-D-Trp-OH --, 51 "H-iD-Glu-D-Trp-OH" should read -- H-γD-Glu-D-Trp-OH --,52 "$C_{16}H_{20}N_3O_5$," should read -- $C_{16}H_{19}N_3O_5$, --, 53 "334.35" should read --333.34 --;

Column 6, Table 1 "H-iD-Glu-D-Trp-OH" should read -- H-γD-Glu-D-Trp-OH --, "H-iL-Glu-D-Trp-OH" should read -- H-γL-Glu-D-Trp-OH --, "Ala-iD-Glu-D-Trp-OH" should read -- Ala-γD-Glu-D-Trp-OH --, "ζ-aminocaproyl-iD-Glu-D-Trp-OH" should read -- ζ-aminocaproyl-γD-Glu-D-Trp-OH --, "H-iD-Glu-D-Trp-Lys" should read -- H-γD-Glu-D-Trp-Lys -- and "Leu-iD-Glu-D-Trp-OH " should read -- Leu-γD-Glu-D-Trp-OH --;

Column 6, Table 2 "iD-Glu-D-Trp" should read -- γD-Glu-D-Trp --;

Column 6, lines 20 "iD-Glu-D-trp" should read -- γD-Glu-D-Trp --, 53 "H-iD-Glu-D-Trp-OH" should read -- H-γD-Glu-D-Trp-OH --, 54 "H-iD-Glu-D-Trp-OH" should read -- H-γD-Glu-D-Trp-OH --;

UNITED STATES PATENT AND TRADEMARK OFFICE
CERTIFICATE OF CORRECTION

PATENT NO. : 5,736,519
APPLICATION NO. : 08/657888
DATED : April 7, 1998
INVENTOR(S) : Vladislav I. Deigin and Andrei Marxovich Korotkov It is certified that error appears in the above-identified patent and that said Letters Patent is hereby corrected as shown below:

Column 7, lines 24 "H-iD-Glu-D-Trp-OH" should read -- H-γD-Glu-D-Trp-OH --, 46 "H-iD-Glu-D-Trp-OH" should read -- H-γD-Glu-D-Trp-OH --, 66 "H-iD-Glu-D-Trp-OH" should read -- H-γD-Glu-D-Trp-OH --;

Column 8, line 42 "H-iD-Glu-D-Trp-OH" should read -- H-γD-Glu-D-Trp-OH --.

Claim 1, Column 9, line 3 "iD-glutamic acid" should read -- γD-glutamic acid --.

Claim 2, Column 9, line 11 "iD-glutamic acid" should read -- γD-glutamic acid --.

Claim 3, Column 9, line 14 "H-iD-Glu-D-Trp-OH" should read
-- H-γD-Glu-D-Trp-OH --.

Signed and Sealed this

Nineteenth Day of December, 2006

JON W. DUDAS
*Director of the United States Patent and Trademark Office*